US006413555B1

(12) United States Patent
Lee

(10) Patent No.: US 6,413,555 B1
(45) Date of Patent: Jul. 2, 2002

(54) COMPOSITION AND METHOD OF TREATING NAIL INFECTIONS

(75) Inventor: Ronald Eugene Lee, Garrettsville, OH (US)

(73) Assignee: All Nature's Solutions L.L.C., Garrettsville, OH (US)

( * ) Notice: Subject to any disclaimer, the term of this patent is extended or adjusted under 35 U.S.C. 154(b) by 0 days.

(21) Appl. No.: 09/751,749

(22) Filed: Dec. 29, 2000

(51) Int. Cl.$^7$ ................................................ A61K 35/78
(52) U.S. Cl. .................... 424/742; 424/725; 424/78.07; 424/405
(58) Field of Search .................. 424/725, 742

(56) References Cited

U.S. PATENT DOCUMENTS 5,620,695 A * 4/1997 Elliott
5,894,020 A * 4/1999 Concha
6,136,329 A * 10/2000 Boratyn

OTHER PUBLICATIONS

Tyler, "Herbs of Choice the Therapeutic Use of Phytomedicinals," 1994, Pharmaceutical Products Press, Haworth Press, Inc., p. 160.*

Peirce, "Practical Guide to Natural Mdeicines," 1999, Stonesong Press, William Morrow and Company, Inc., pp. 390–392.*

"PDR for Herbal Medicine," 1998, First Edition, Medical Economics Company, pp. 836–839.*

* cited by examiner

Primary Examiner—Leon B. Lankford, Jr.
Assistant Examiner—Ruth A. Davis
(74) Attorney, Agent, or Firm—James A. Lucas; Driggs, Lucas, Brubaker & Hogg Co., LPA

(57) ABSTRACT

Infections of toe nails and finger nails caused by fungi and yeast are treated topically by applying a liquid mixture of natural ingredients to the infected area. The mixture includes the essential oils of between about 10 and about 17 ml. of tea tree; between about 10 and about 17 ml. of lavender oil, and between about 1 and about 3.5 ml. of eucalyptus oil in a total of 30 ml. of liquid. All of the ingredients preferably are pharmaceutical grade for the best results. The liquid mixture is typically applied to the affected area once or twice a day for a period of at least two months until the infection is cured. A few drops of the composition can also be placed into the toe box of shoes and the toe portion of slippers when not being worn to prevent re-infection.

8 Claims, 2 Drawing Sheets

(a) (b)

COMPOSITION AND METHOD OF TREATING NAIL INFECTIONS

FIELD OF THE INVENTION

The present invention relates to the treatment of fungal and yeast infections of the nails on the hands and the toes and to topical formulations that are useful for such treatment.

BACKGROUND OF THE INVENTION

A common problem affecting many people is an infection called Onychomycosis caused by fungi and yeast that attack nails, and particularly toe nails. Fungi called dermatophytes are the most frequent cause of invasion of the nail. The fungi feed off the nail protein called keratin. Although the fungi are unsightly, and turns the toe nails scaly, yellow, brown or black, some people have no discomfort from the infection and, in fact, live with the condition for years and even decades. For others, however, the infection can adversely affect the quality of life when it is accompanied by itching, swelling, and general irritation. It can also lead to more serious complications including secondary bacterial infections. For instance, when an individual has impaired circulation to the feet, common among diabetics, the damage done by the fungus can permit a bacterial infection to begin in the feet. This infection may result in foot and ankle ulcers, may lead to blood poisoning and, in some cases, can lead to gangrene, thereby necessitating amputation of the foot or leg.

The most frequently isolated dermatophyte is called Trichophyton rubrum. It is caused by organisms that are present everywhere. These organisms may be picked up by the feet from the floor of commonly shared bathrooms, decks of swimming pools, beaches, by walking barefoot, or by direct contact with another carrier of the organism. Other ways of contracting the infection are through the shared use of towels, soap and cosmetics. Also, they may be spread through the improper cleaning of dermatology equipment at nail salons. Even new shoes and slippers may carry the organism. The use of an anti-fungal soap for bathing, and thoroughly drying feet and hands after bathing, can help to reduce the likelihood of contamination.

In the United States alone, it is believed that between three and five percent of the population is affected by nail fungus. Based on a total population of 200 million, this means that between 6 and 10 million people are affected. The problem used to be one that mostly affected older persons who were unable to properly cleanse and dry their feet. Now, however, nail fungus is infecting all age groups. Nail technicians and nail salons do not understand the fungus problem or how is transmitted. If equipment is not disinfected between customers, this may cause the nail infection to spread from one person to another. Furthermore, artificial nails provide a perfect environment for the growth of fungi.

The infection caused by these fungi is called onychomycosis. Onychomycosis has been found to be quite resistant to most forms of treatment. The nail infections reside in an area that is difficult to access by conventional topical treatment, and antifungal drugs cannot readily penetrate the nail plate to reach the infection sites under the nail. Therefore, onychomycosis has traditionally been treated by oral administration of antifungal drugs. This is undesirable due to the potential side effects of such drugs. Blood tests may be required to make sure that the drug can be tolerated. Furthermore, the various organisms are able to mutate in response to treatment with drugs and to rapidly become resistant to the existing drug treatment. This, of course, requires the expenditure of substantial sums of money for additional research to develop new drugs that will neutralize the mutant strains. To further exacerbate the situation is the realization that many health insurance companies regard such treatment of onychomycosis as cosmetic and, therefore, do not pay for them.

In other instances, surgical removal of the nail may be required prior to the application of topically active antifungal drugs. The drawbacks of surgical procedures are well-known. In addition to the pain and discomfort associated with the removal of the nails, the person is inconvenienced for a certain period of time while the nail grows back.

Among health-care products are many medications that are labeled as 'natural'. But despite their label, these medications contain no more than a minimal amount of ingredients that could truly be labeled as non-chemical. Instead, the treatment of topical infections with chemical medications is the method of choice within the medical and cosmetology professions.

The use of natural skin care products is based on herbs and natural oils to treat these topical infections. This treatment is much more cost-effective than is the use of pharmaceuticals. Clearly, a topical formulation having antifungal activity and that can be applied topically once or twice daily would be advantageous. Even more so would be such a product that contains no harmful chemicals or drugs.

BRIEF SUMMARY OF THE INVENTION

The present invention relates to a new composition that has been found to be highly efficient in treating fungal, bacterial and viral infections of toe and finger nails. The composition consists of a liquid composition consisting essentially of the following ingredients: between about 10 and about 17 ml., of tea tree essential oil; between about 10 and about 17 ml. of lavender essential oil, and between about 1 and about 3.5 ml. of eucalyptus essential oil in a total of 30 ml. of liquid. All of the ingredients preferably are pharmaceutical grade for best results.

The invention also relations to a topical dressing which is composed of a mixture of essential oils comprising between about 10 and about 17 ml. of tea tree essential oil, between about 10 and about 17 ml. of lavender essential oil, and between about 1 and about 3.5 ml. of eucalyptus essential oil in a total of 30 ml. of liquid. All of the ingredients in the topical dressing preferably are pharmaceutical grade. The tea tree essential oil preferably is present in an amount between about 12 and about 15 ml. and, more specifically, in an amount of about 13.5 ml. The lavender essential oil preferably is present in an amount of between about 12 and about 15 ml. and, more specifically, 13.5 ml. The eucalyptus essential oil preferably is present in an amount of between about 1 and about 3.5 ml.

The invention furthermore relates to a method of treating fungal and yeast infections of toe and finger nails comprising applying a mixture of essential oils to the nails and cuticles, said mixture consisting essentially of between about 10 and about 17 ml., preferably between about 12 and about 15 ml. and, more preferably, about 13.5 of tea tree essential oil; between about 10 and about 17 ml., preferably between about 12 and about 15 ml., and, more preferably, about 13.5 of lavender essential oil, and between about 1 and about 3.5 ml., preferably about 3 ml., of eucalyptus essential oil in a total of 30 ml. of liquid. Preferably, all of the ingredients in the mixture are pharmaceutical grade.

The invention also includes the method of preventing infection of toe nails by yeast and fungal infections comprising the step of placing a small quantity of the composition consisting essentially of between about 10 and about 17 ml. of tea tree essential oil; between about 10 and about 17 ml. of lavender essential oil, and between about 1 and about 3.5 ml. of eucalyptus essential oil in a total of 30 ml. of liquid into the toe portion of shoes and slippers when not being worn. The small quantity of the composition preferably is absorbed on a cotton ball which is then placed into the toe portion of a shoe or slipper.

DETAILED DESCRIPTION OF THE PRESENT INVENTION

Figure 1:
FIG. 1 shows the related art results of in vitro fungal activity.

This invention relates to a topical composition for the treatment of yeast and fungal infections of the nails of the toes and the fingers. The invention also relates to the method of preparing the composition and for treating such infections.

The composition comprises a mixture of three essential oils, lavender oil, tea tree oil and eucalyptus oil in a ratio that his been found to be highly effective in the treatment of various types of onychomycosis. The oils are present in the following approximate amounts, based on a 30 ml. quantity:

|  | broad range | intermediate range | narrow range |
| --- | --- | --- | --- |
| Lavender oil: | 10–17 ml. | 12–15 ml. | 13.5 ml. |
| Tea tree oil: | 10–17 ml. | 12–15 ml. | 13.5 ml. |
| Eucalyptus oil: | 1–3.5 ml. | 1–3.5 ml. | 3 ml. |

All of the oils are essential oils, containing less than 1% moisture and impurities. It has been found that the activity of the pharmaceutical grade of these oils in the mixture is higher than the activities of the less pure grades.

Lavender is known for its ability to promote healing and reduce scarring, and to promote new skin growth. It helps to draw blood to the site to enhance circulation and to increase healing. The pharmaceutical grade of the essential oil is available from Europe.

Eucalyptus is a mild anti-inflammatory, and helps to dissipate heat. Thus, when applied topically, it has been found to slow down or reverse the spread of the infection. The pharmaceutical grade of this essential oil is available from suppliers in Australia.

Tea tree is recognized for its ability to promote healing in a very broad range of bacterial, fungal and viral infections. The pharmaceutical grade is available from suppliers in Australia.

All three of these oils can be obtained domestically from Creation Herbal Products in Boone, N.C.

The composition of the present invention is prepared by measuring and then pouring the individual oils in a clean blender and thoroughly blending or shaking them together. The oils do not coagulate when mixed together. No heat is required for the blending step. The oils appear to retain their individual identity without the occurrence of a chemical reaction. However, the mixture clearly shows synergism when used for the treatment of the fungi and yeast that commonly cause onychomycosis.

The treatment should begin with trimming the infected nail or nails back as far as practical, followed by the use of an emery board or small grinder to file the surface of the nail as thin as possible. Precautions should be taken to avoid filing or grinding through the nail into the skin. One or two drops of the composition is then applied to the cuticle of each infected nail. The nail should then be allowed to thoroughly dry before inserting the feet into socks and shoes. The formulation is applied at least once, and preferably twice daily, preferably after showering or bathing. The treatment should be continued until the infection has been completely arrested. For badly infected nails, it is necessary to continue the treatment for as long as it takes to grow out a new nail. This time frame can vary depending on a number of factors, including genetic makeup, personal hygiene and diet. Furthermore, it usually takes considerably longer to cure toe nails than it does to cure finger nails. A treatment period of at least two, but more typically four to 12 months is to be expected.

Yeast and fungal spores that cause these infections remain in shoes and slippers. To minimize the chances of re-infection, a few drops of the formulation of the present invention can be placed in the toe portion of all pairs of shoes and slippers when they are not being worn. This can be done by putting the mixture on a cotton ball which is then placed in the toe box of the shoe or the toe of the slipper until they are once again worn.

The following examples are presented for the purpose of comparing the present composition to the closest art deemed to be relevant.

EXAMPLE 1

A mixture of 20 ml. tea tree oil, 6 ml. of lavender oil and 4 ml. of eucalyptus oil was prepared. All of the ingredients were pharmaceutical grade essential oils. The antifungal properties were tested by microbial challenge with mixed culture of the following pure freshly isolated organisms:

Yeast: Candida albicans, Candida tropicalis, Candida glabrata and Candida parapsolosis.

Fungi: Trichophyton rubrum

This untreated culture is shown in FIG. 1a.

The organisms were streaked on a confluent growth pattern on designated media. The results are noted in FIG.1b, wherein a zone of inhibition of 80–85% is evident on the test media.

EXAMPLE 2

A mixture of 13.5 ml. of tea tree oil, 13.5 ml. of lavender oil and 35 ml. eucalyptus oil was prepared and was tested on the same pure freshly isolated organisms as for Example 1, namely Yeasts: Candida albicans, Candida tropicalis, Candida glabrata and Candida parapsolosis.

Fungi: Trichophyton rubrum

Figure 2:
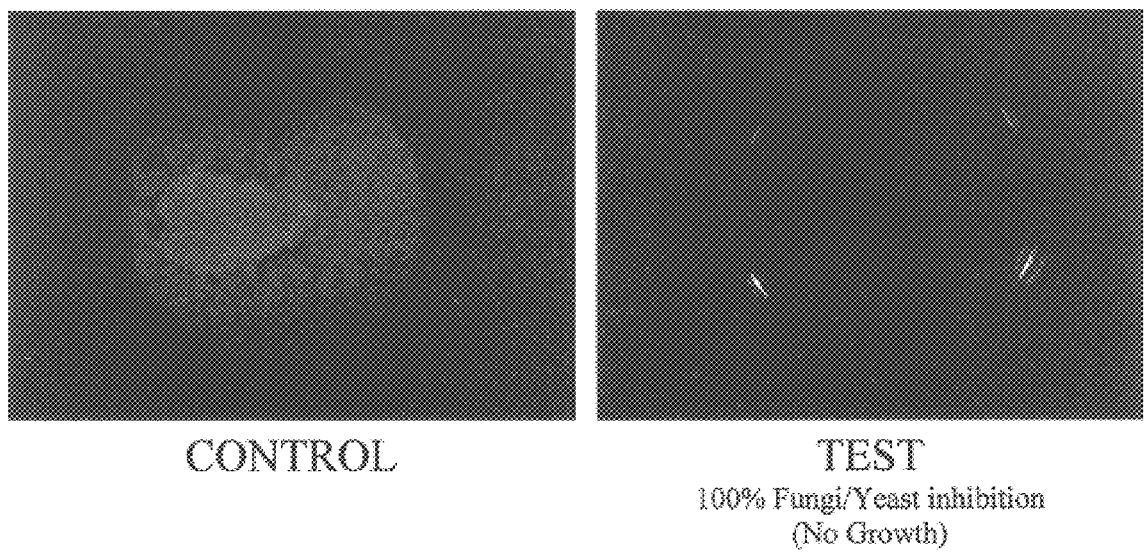
FIG. 2 shows the in vitro fungal activity of the present invention.

This untreated culture is shown in FIG. 2a.

As in Example 1, the organisms were streaked on a confluent growth pattern on designated media. As noted in FIG. 2b, a zone of inhibition of 100% is evident on the test media. The appearance of the untreated culture of FIG. 2a is different than that of FIG. 1a due to the fact that the tests were done at different times and were photographed under different lighting conditions.

While the invention has been described in combination with embodiments thereof, it is evident that many alternatives, modifications, and variations will be apparent to those skilled in the art in light of the foregoing teachings.

For example, satisfactory results can be achieved using the blend of these essential oils even though one or more of the oils may not be pharmaceutical grade. Accordingly, the invention is intended to embrace all such alternatives, modifications and variations as fall within the spirit and scope of the appended claim.

What is claimed is:

1. A liquid composition for treating Onychomycosis consisting essentially of the following ingredients:
   a) between about 10 and about 17 ml. of tea tree essential oil;
   b) between about 10 and about 17 ml. of lavender essential oil, and
   c) between about 1 and about 3.5 ml. of eucalyptus essential oil in a total of 30 ml. of liquid.

2. The composition according to claim 1 wherein all of the essential oils are pharmaceutical grade.

3. The composition according to claim 2 wherein the tea tree essential oil is present in an amount between about 12 and about 15 ml., the lavender essential oil is present in an amount of between about 12 and about 15 ml., and the eucalyptus essential oil is present in an amount of between about 1 and about 3.5 ml.

4. The composition according to claim 3 wherein the tea tree essential oil is present in an amount of about 13.5 ml., the lavender essential oil is present in an amount of about 13.5 ml., and the eucalyptus essential oil is present in an amount of about 3 ml.

5. A topical dressing comprising a mixture of essential oils comprising:
   a) between about 10 and about 17 ml. of tea tree essential oil;
   b) between about 10 and about 17 ml. of lavender essential oil, and
   c) between about 1 and about 3.5 ml. of eucalyptus essential oil in a total of 30 ml. of liquid.

6. The topical dressing according to claim 5 wherein all of the essential oils are pharmaceutical grade.

7. The topical dressing according to claim 6 wherein the tea tree essential oil is present in an amount between about 12 and about 15 ml.; the lavender essential oil is present in an amount of between about 12 and about 15 ml.; and the eucalyptus essential oil is present in an amount of between about 1 and about 3.5 ml.

8. The topical dressing according to claim 7 wherein the tea tree essential oil is present in an amount of about 13.5 ml.; the lavender essential oil is present in an amount of about 13.5 ml.; and the eucalyptus essential oil is present in an amount of about 3 ml.

* * * * *